(12) United States Patent
Zhao et al.

(10) Patent No.: US 11,517,184 B2
(45) Date of Patent: Dec. 6, 2022

(54) SYSTEMS AND METHODS OF REGISTRATION FOR IMAGE-GUIDED PROCEDURES

(71) Applicant: INTUITIVE SURGICAL OPERATIONS, INC., Sunnyvale, CA (US)

(72) Inventors: Tao Zhao, Sunnyvale, CA (US); Federico Barbagli, San Francisco, CA (US); Timothy D. Soper, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 506 days.

(21) Appl. No.: 16/481,990

(22) PCT Filed: Jan. 31, 2018

(86) PCT No.: PCT/US2018/016295
§ 371 (c)(1),
(2) Date: Jul. 30, 2019

(87) PCT Pub. No.: WO2018/144636
PCT Pub. Date: Aug. 9, 2018

(65) Prior Publication Data
US 2020/0229679 A1 Jul. 23, 2020

Related U.S. Application Data

(60) Provisional application No. 62/453,380, filed on Feb. 1, 2017.

(51) Int. Cl.
*A61B 1/005* (2006.01)
*A61B 34/20* (2016.01)
(Continued)

(52) U.S. Cl.
CPC ........ *A61B 1/0051* (2013.01); *A61B 1/00009* (2013.01); *A61B 1/0016* (2013.01);
(Continued)

(58) Field of Classification Search
CPC .... A61B 2034/2061; A61B 2562/0247; A61B 2562/0261; A61B 5/08; A61B 2034/2051;
(Continued)

(56) References Cited

U.S. PATENT DOCUMENTS 8,343,037 B2 1/2013 Ishihara
2004/0176683 A1 9/2004 Whitin et al.
(Continued)

FOREIGN PATENT DOCUMENTS

CN 104717913 A 6/2015
JP 2008220672 A 9/2008
(Continued)

OTHER PUBLICATIONS

International Search Report and Written Opinion for application No. PCT/US2018/016295, dated May 10, 2018, 11 pages.
(Continued)

*Primary Examiner* — Aaron B Fairchild
(74) *Attorney, Agent, or Firm* — Haynes and Boone, LLP

(57) ABSTRACT

A medical device includes an elongate device and one or more processors coupled to the elongate device. The elongate device includes a steerable distal end and a shape sensor located along a length of the elongate device. While the elongate device is being traversed through one or more passageways of a patient, the one or more processors are configured to, based on information from a sensor, monitor an insertion motion of the elongate device, detect a data collection event, and capture, in response to detecting the data collection event, a plurality of points along the length of the elongate device using the shape sensor. The data (Continued)

collection event is at least partially based on a change in direction of the insertion motion of the elongate device.

20 Claims, 10 Drawing Sheets

(51) Int. Cl.
*A61B 1/00* (2006.01)
*A61B 1/04* (2006.01)
*A61B 1/267* (2006.01)

(52) U.S. Cl.
CPC ...... *A61B 1/00154* (2013.01); *A61B 1/00165* (2013.01); *A61B 1/042* (2013.01); *A61B 1/267* (2013.01); *A61B 34/20* (2016.02); *A61B 2034/2061* (2016.02); *A61B 2505/05* (2013.01); *A61B 2562/0247* (2013.01); *A61B 2562/0261* (2013.01)

(58) Field of Classification Search
CPC ............ A61B 2090/064; A61B 1/0051; A61B 1/00009; A61B 1/00154; A61B 1/0016; A61B 1/00165; A61B 1/042; A61B 1/267; A61B 34/20; A61B 2505/05; A61B 2034/105; A61B 2034/2059; A61B 34/37; A61B 2017/00809; A61B 2090/3614; A61B 1/00156
See application file for complete search history.

(56) References Cited

U.S. PATENT DOCUMENTS

| | | | | |
|---|---|---|---|---|
| 2009/0137952 | A1* | 5/2009 | Ramamurthy | A61B 1/00045 604/95.01 |
| 2010/0113876 | A1* | 5/2010 | Ishihara | G02B 23/2476 600/117 |
| 2010/0274389 | A1* | 10/2010 | Ortmaier | A61B 34/30 700/258 |
| 2013/0060082 | A1* | 3/2013 | Sano | A61B 5/062 600/103 |
| 2014/0330080 | A1 | 11/2014 | Laby et al. | |
| 2015/0265368 | A1* | 9/2015 | Chopra | A61B 1/00009 600/587 |
| 2019/0328211 | A1* | 10/2019 | Tezuka | A61B 1/31 |

FOREIGN PATENT DOCUMENTS

| | | |
|---|---|---|
| JP | 2013508058 A | 3/2013 |
| JP | 2013534433 A | 9/2013 |
| JP | 2015119772 A | 7/2015 |
| JP | 2016505279 A | 2/2016 |
| JP | 2020503134 A | 1/2020 |
| WO | WO-2012158325 A2 | 11/2012 |
| WO | WO-2014028400 A1 | 2/2014 |
| WO | WO-2015061756 A1 | 4/2015 |
| WO | WO-2016077419 A1 | 5/2016 |
| WO | WO-2016164311 A | 10/2016 |
| WO | WO-2016191298 A1 | 12/2016 |
| WO | WO-2017030913 A2 | 2/2017 |
| WO | WO-2018127522 A1 | 7/2018 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18747545.4 dated Oct. 22, 2020, 7 pages.
International Preliminary Reporton Patentability for Application No. PCT/US2018/016295, dated Aug. 15, 2019, 10 pages.

* cited by examiner

SYSTEMS AND METHODS OF REGISTRATION FOR IMAGE-GUIDED PROCEDURES

RELATED APPLICATIONS

This patent application is a U.S. National Stage patent application of International Patent Application No. PCT/US2018/016295 filed on Jan. 31, 2018, the benefit of which is claimed, and claims priority to and benefit of the filing date of U.S. Provisional Patent Application No. 62/453,380, entitled "Systems and Methods of Registration for Image-Guided Surgery," filed Feb. 1, 2017, each of which is incorporated by reference herein in its entirety.

FIELD

The present disclosure is directed to systems and methods for conducting an image-guided procedure, and more particularly to registration during an image-guided procedure.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. Traditional instrument tracking and referencing systems may require the use of patient pads during pre-operative and operative imaging and may disturb the clinical environment or workflow. Systems and methods for performing image-guided surgery with minimal clinical disturbances are needed.

SUMMARY

The embodiments of the invention are best summarized by the claims that follow the description.

Consistent with some embodiments, a medical device being capable of capturing location data for passageways within a patient, such as airways of the lungs, uses a shape sensor that identifies various points along its length. By mounting the shape sensor along the length of an elongate device and inserting the elongate device into the passageways to a desired location, the shape senor may be used to determine the location of points along the passageways where the elongate device is inserted. The location of the points can then be matched up with corresponding points from a model of the passageways obtained using medical imaging (e.g., x-rays, computed tomography (CT), magnetic resonance imaging (MRI), and/or the like) in order to guide an operator in inserting the elongate device to a target location within the passageways.

Consistent with some embodiments, a medical device includes an elongate device including a steerable distal end and a shape sensor located along a length of the elongate device and one or more processors coupled to the elongate device. While the elongate device is being traversed through one or more passageways of a patient, the one or more processors are configured to detect a data collection event, and capture, in response to detecting the data collection event, a plurality of points along the length of the elongate device using the shape sensor.

Consistent with some embodiments, a method includes an elongate device including a steerable distal end and a shape sensor located along a length of the elongate device, and one or more processors coupled to the elongate device. While the elongate device is being traversed through one or more passageways of a patient, the one or more processors are configured to monitor an insertion motion of the elongate device, detect a data collection event, and capture, in response to detecting the data collection event, a plurality of points along the length of the elongate device using the shape sensor. The data collection event is at least partially based on the insertion motion of the elongate device.

Consistent with some embodiments, a non-transitory machine-readable medium includes a plurality of machine-readable instructions which when executed by one or more processors associated with a medical device are adapted to cause the one or more processors to perform a method. The method includes monitoring an insertion motion of an elongate device while the elongate device is being traversed through one or more passageways of a patient. The elongate device has a steerable distal end and a shape sensor located along a length of the elongate device. The method further includes detecting a data collection event, wherein the data collection event is at least partially based on the insertion motion of the elongate device and capturing, in response to detecting the data collection event, a plurality of points along the length of the elongate device using the shape sensor.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 5A:
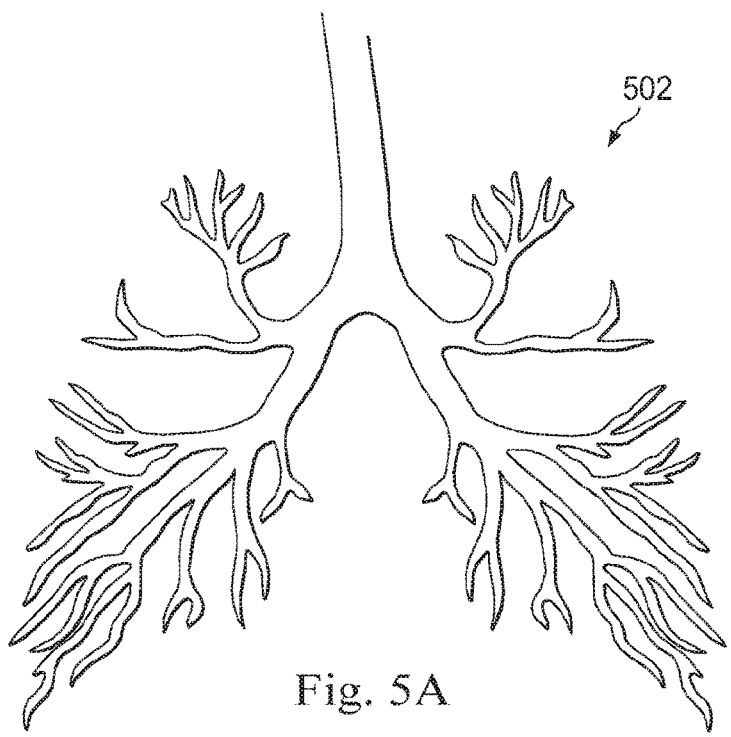
Figure 5B:
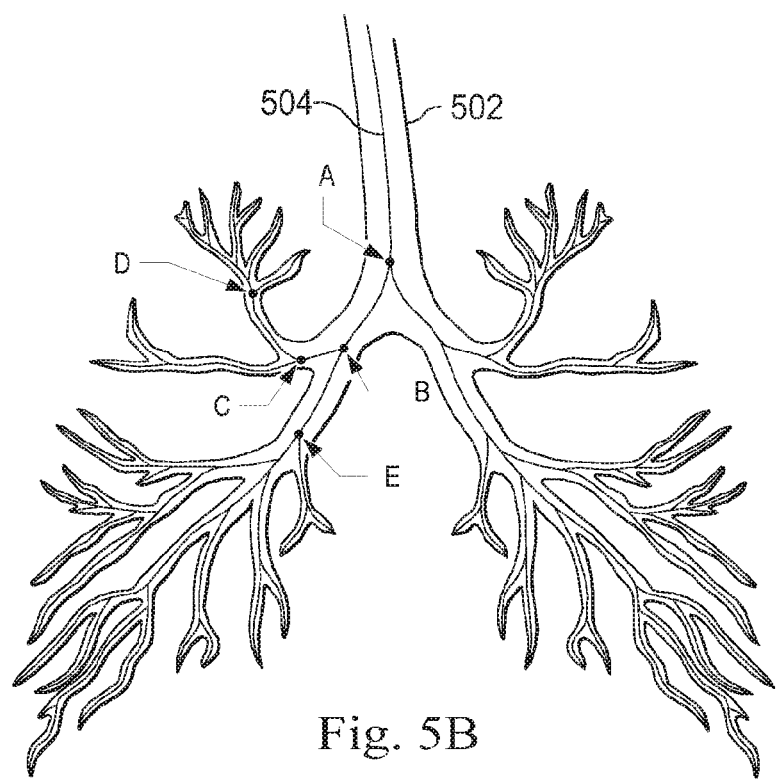
Figure 5C:
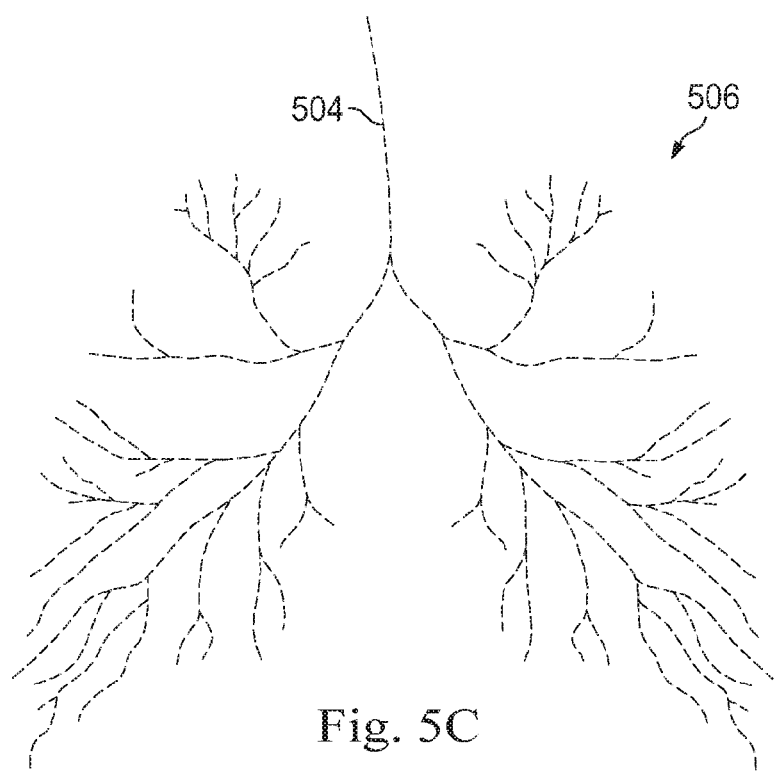

FIGS. 5A, 5B, and 5C illustrate exemplary application of processes in a segmentation method that generates a model of human lungs for registration.

Figure 6A:
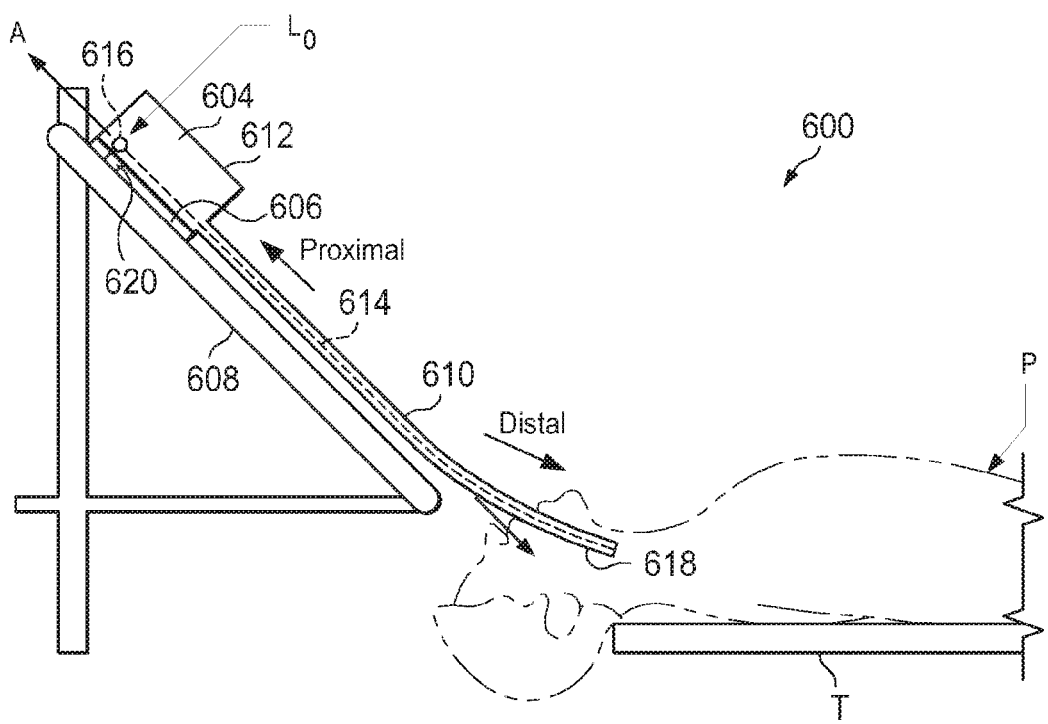
Figure 6B:
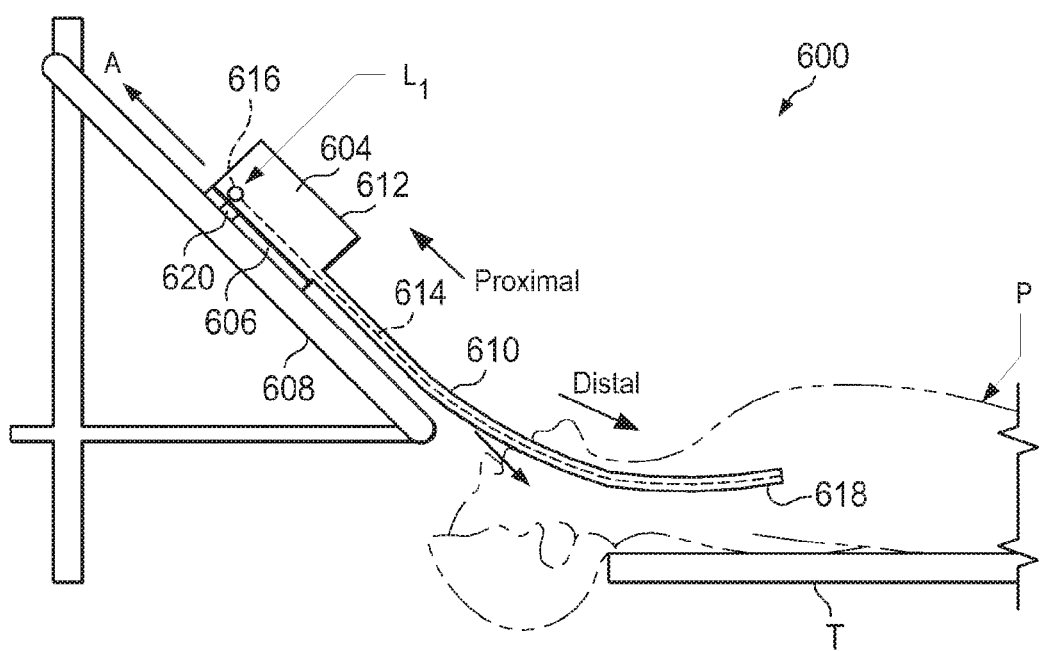

FIGS. 6A and 6B are exemplary side views of a patient coordinate space including a medical instrument mounted on an insertion assembly.

Figure 6C:
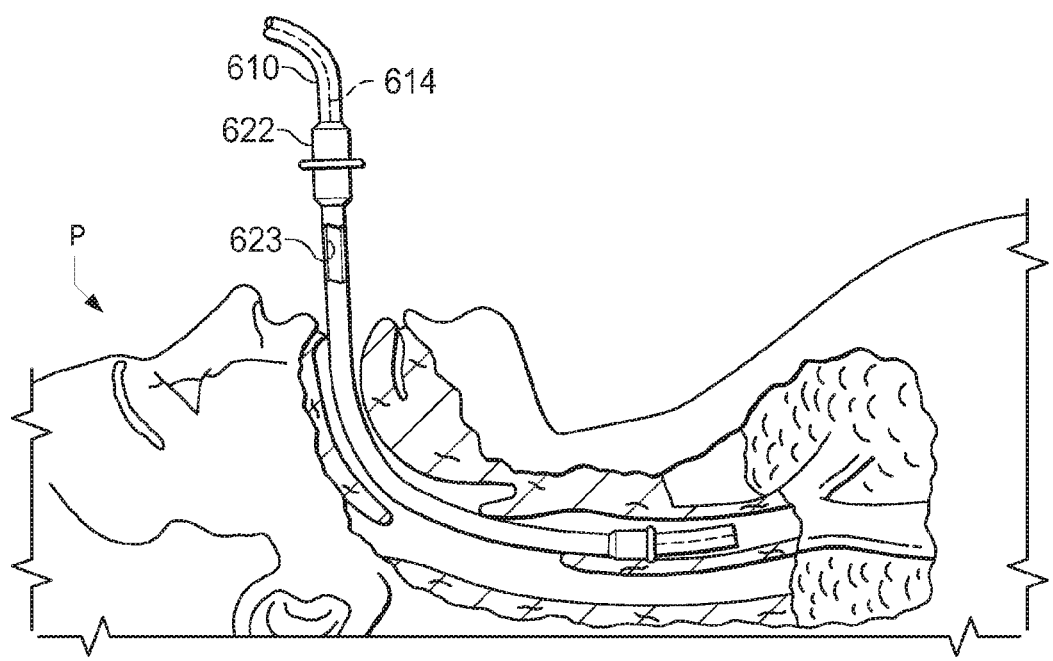

FIG. 6C is an exemplary side view of a patient in a patient coordinate space including an endotracheal tube.

Figure 7:
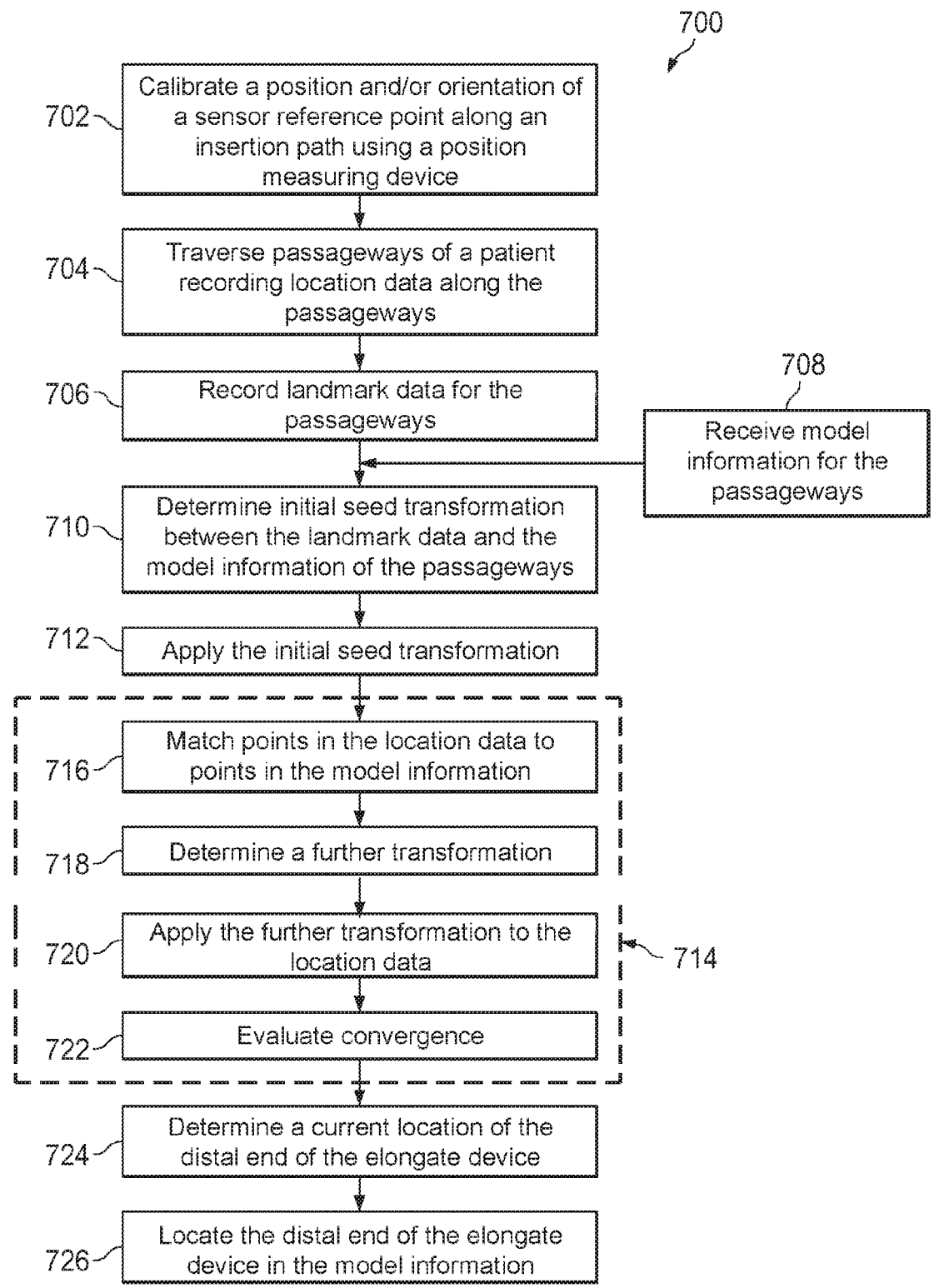

FIG. 7 illustrates a flowchart of an exemplary method of providing guidance for an image-guided surgical procedure.

Figure 8:
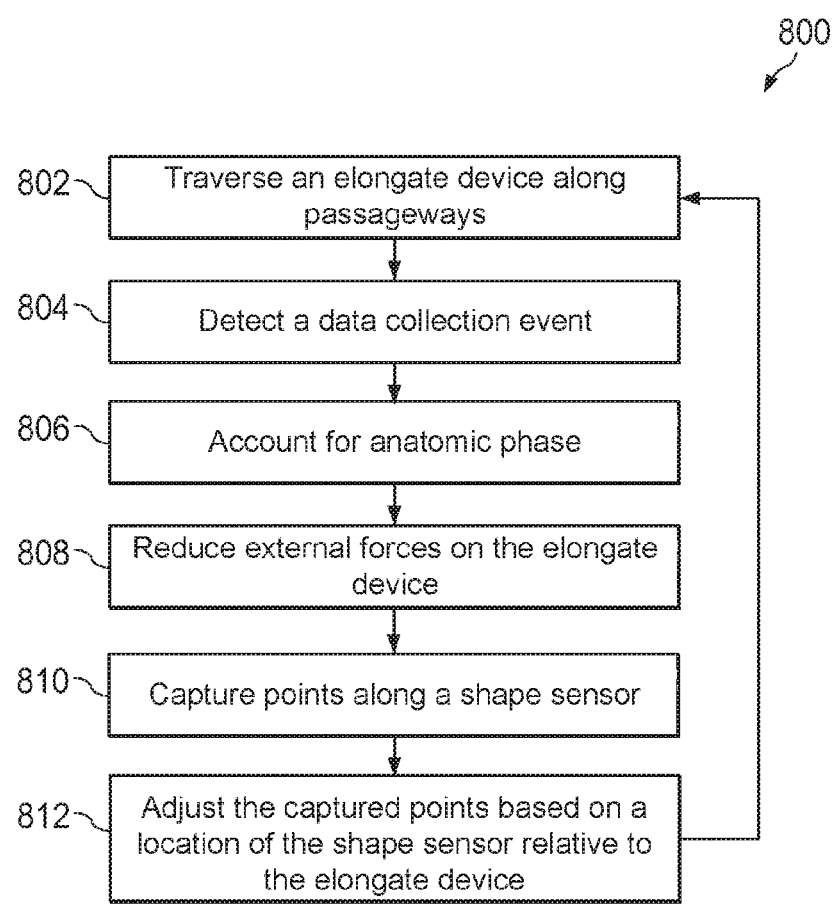

FIG. 8 illustrates a flowchart of an exemplary method of recording passageway location data.

Figure 9:
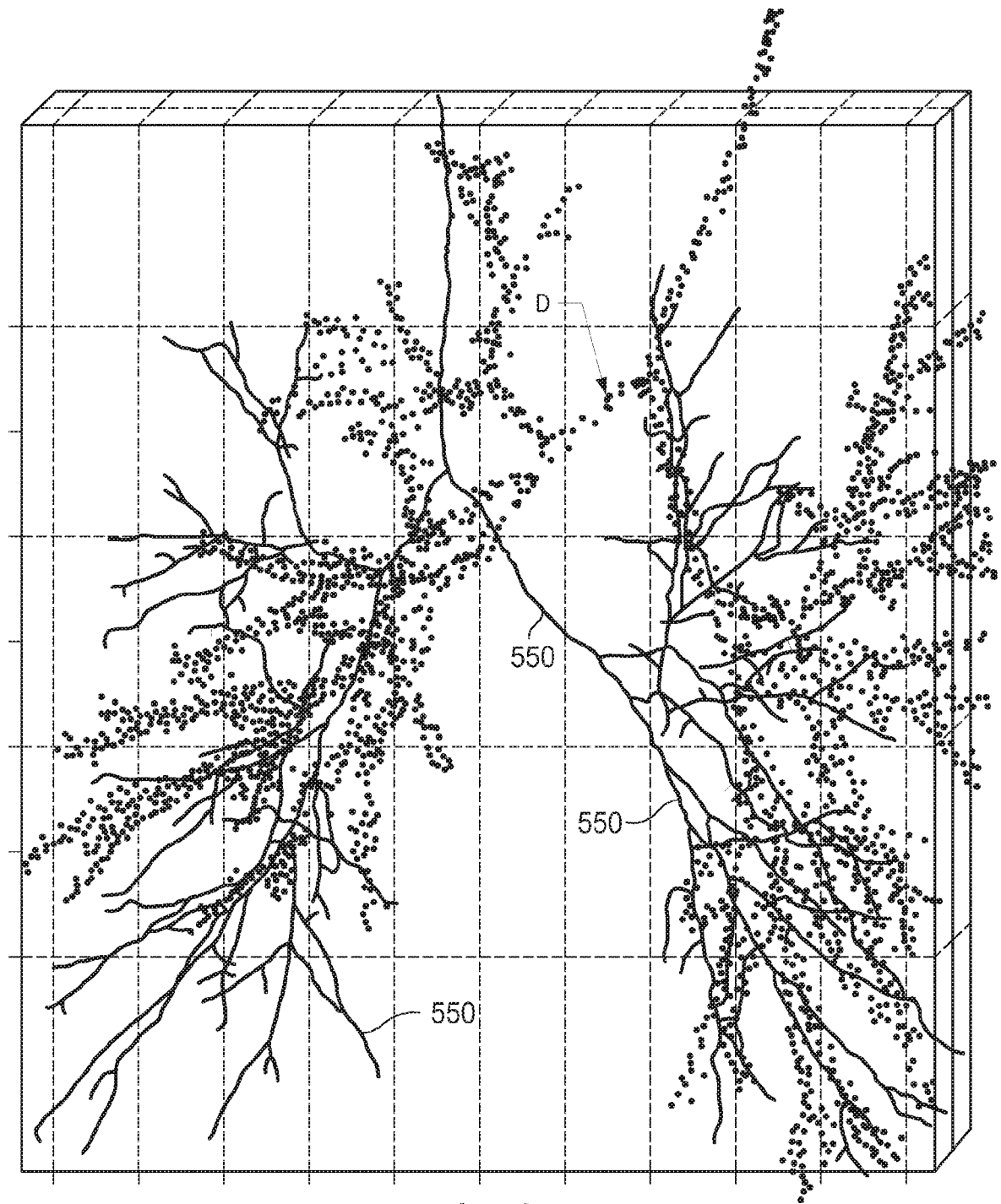

FIG. 9 illustrates exemplary location data collected by traversing airways in human lungs.

Figure 10:
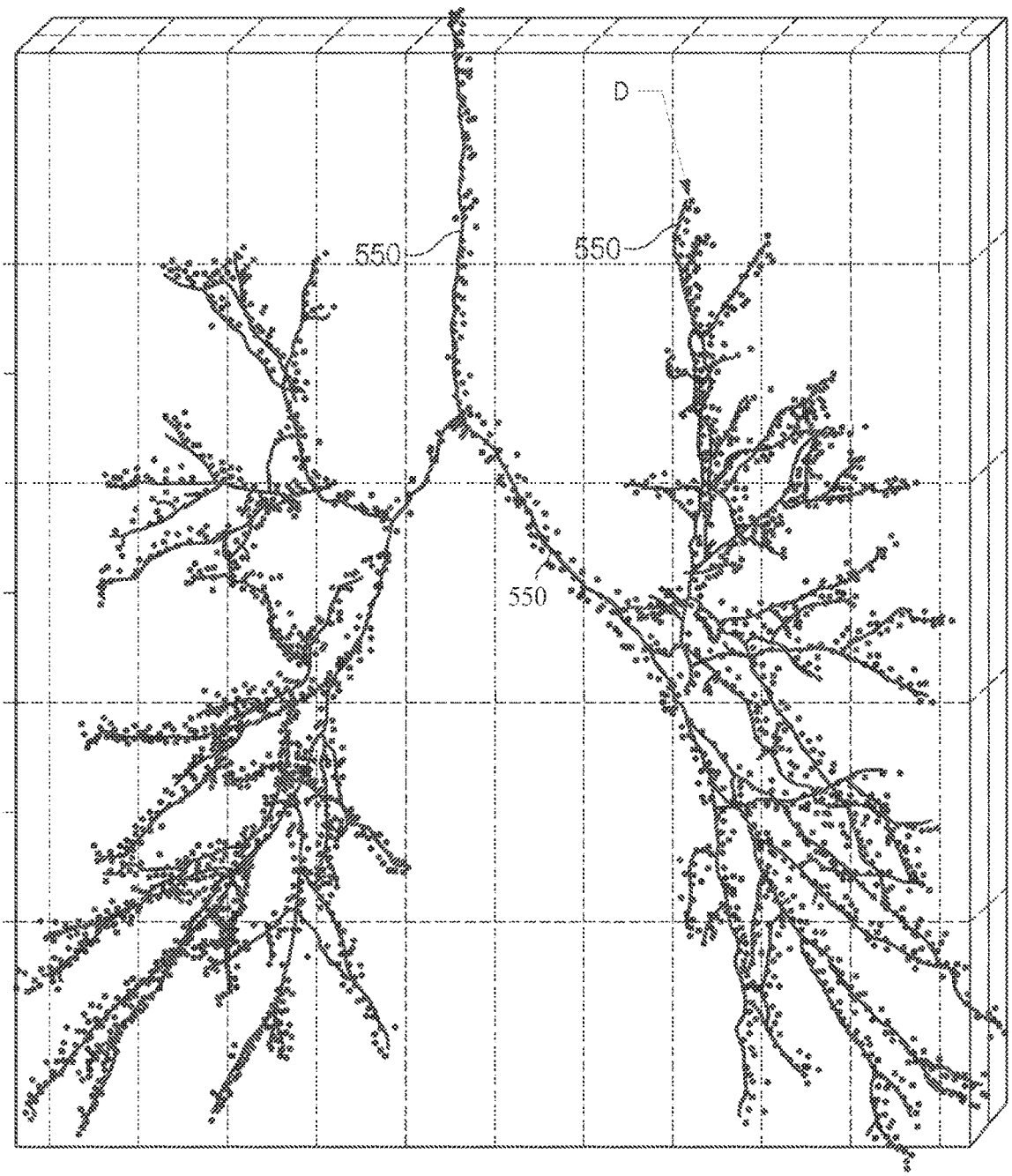

FIG. 10 illustrates an exemplary post registration alignment of two sets of points resulting from application of an exemplary registration technique.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

This disclosure focuses primarily on embodiments where the passageways being traversed are airways in lungs. However, one of ordinary skill in the art would understand that these disclosures are equally applicable to other types of passageways that include one or more branch points. For example, other suitable anatomic passageways include vasculature, renal calyces, lymphatic vessels, and/or the like. In other examples, the passageways may correspond to non-anatomic passageways including sewer tunnels, plumbing pipes, conduits, heating ventilation and air conditioning (HVAC) ducts, mines, caves, and/or the like.

Figure 1:
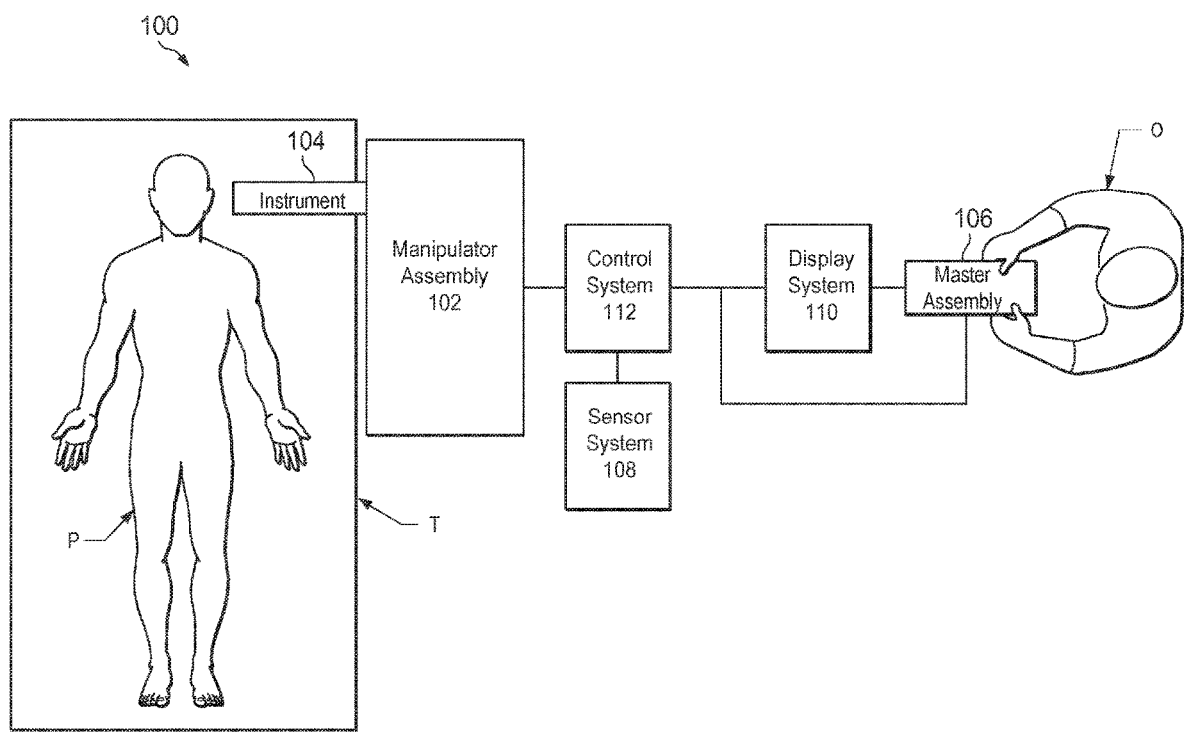
FIG. 1 is an exemplary teleoperated medical system.

FIG. 1 is an exemplary teleoperated medical system 100. In some embodiments, teleoperated medical system 100 may be suitable for use in, for example, surgical, diagnostic, therapeutic, or biopsy procedures. As shown in FIG. 1, medical system 100 generally includes a manipulator assembly 102 for operating a medical instrument 104 in performing various procedures on a patient P. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102.

Master assembly 106 may be located at a operator's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images. , such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one non-teleoperational manipulator assembly, more than one teleoperational manipulator assembly, and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2A:
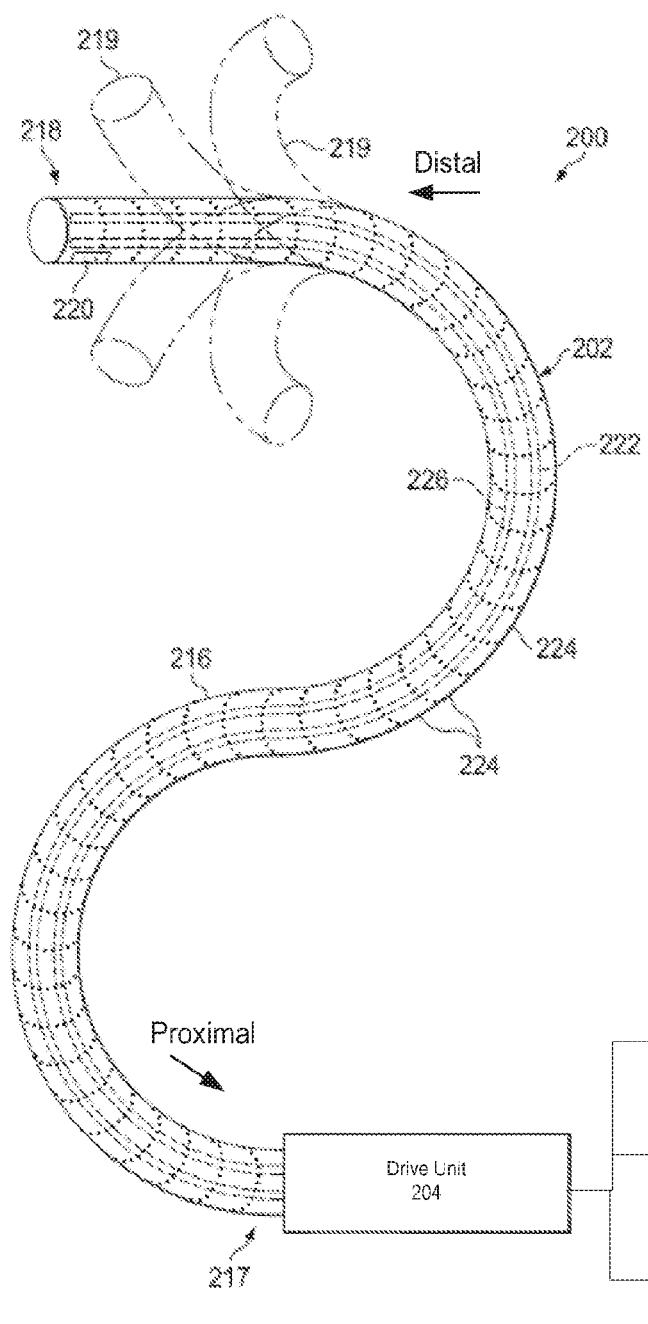
FIG. 2A illustrates an exemplary medical instrument system.

FIG. 2A is an exemplary medical instrument system 200. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Figure 2B:
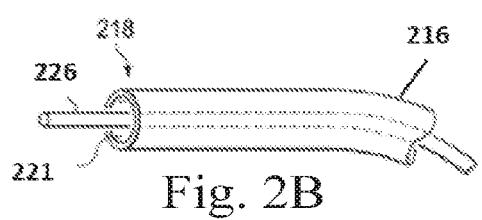
FIG. 2B illustrates an exemplary medical instrument with an extended medical tool.

Flexible body 216 includes a channel 221 sized and shaped to receive a medical instrument 226. FIG. 2B is an exemplary flexible body 216 with medical instrument 226 extended. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sept. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3:
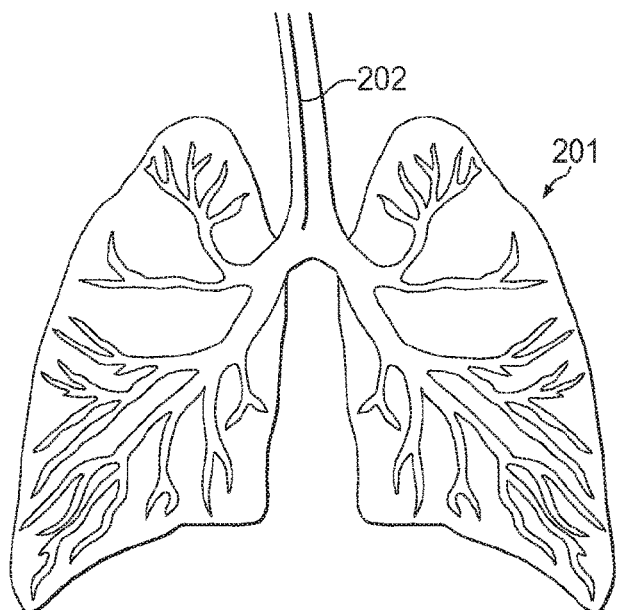
FIG. 3 illustrates an exemplary medical instrument positioned within an anatomic passageway of a human lung.

FIG. 3 illustrates an exemplary medical instrument in the form of elongate device 202 positioned within an anatomic passageway of a human lung 201. In some embodiments, elongate device 202 may be used in other passageways of an anatomy.

Figure 4:
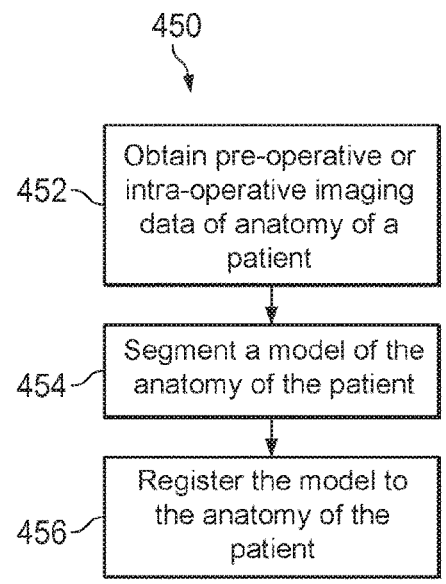
FIG. 4 illustrates a flowchart of an exemplary method to provide guidance in an image-guided surgical procedure.

FIG. 4 illustrates a flowchart of an exemplary method 450 for use in an image-guided surgical procedure. At process 452, pre-operative or intra-operative image data of the anatomy of a patient is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent human lungs 201 of FIG. 3.

At a process 454, a segmented model of the anatomy of the patient is determined. Using computer software alone or in combination with manual input the recorded images are converted into a segmented two-dimensional or three-dimensional composite representation or model of a partial or an entire anatomic organ or anatomic region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as a marching cube function, to generate a 3D surface that encloses the voxels. In some examples, the model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At a process 456, the model is registered to the patient anatomy. In some examples, the registering may occur prior to and/or during the course of an image-guided surgical procedure on the patient. Generally, registration involves the matching of measured points to points of the model through the use of rigid and/or non-rigid transforms. Measured points may be generated using landmarks in the anatomy, electromagnetic coils scanned and tracked during the procedure, and/or a shape sensor system. The measured points may be generated for use in an iterative closest point (ICP) technique as described in further detail below. Other point set registration methods may also be used in registration processes within the scope of this disclosure.

Other registration methods for use with image-guided surgery often involve the use of technologies based on electromagnetic or impedance sensing. Metallic objects or certain electronic devices used in the surgical environment may create disturbances that impair the quality of the sensed data. Other methods of registration may obstruct the clinical workflow. The systems and methods described below may perform registration based upon ICP, or another point set registration algorithm, and the calibrated movement of a point gathering instrument with, for example, a fiber optic shape sensor, thus eliminating or minimizing disruptions in the surgical environment. However, it should be understood that in certain procedures and/or environments, the use of technologies such as electromagnetic sensing, impedance sensing, optical trackers, and/or the like may be desirable as a supplement and/or an alternative to the systems and methods described herein. Other registration techniques may be used to register a set of measured points to a pre-operative model or a model obtained using another modality.

FIGS. 5A, 5B, and 5C illustrate exemplary application of processes in a segmentation method that generates a model of human lungs for registration. In some embodiments, the processes of FIGS. 5A, 5B, and/or 5C may correspond to portions of processes 452 and/or 454 of FIG. 4. FIG. 5A illustrates segmented model 502 of a set of anatomic passageways created from pre-operative or intra-operative imaging data. As shown, the passageways are airways of a human lung. Due to naturally occurring limitations or to limitations set by an operator, segmented model 502 may not include all of the passageways present within the human lungs. For example, relatively narrow and/or distal passageways of the lungs may not be fully included in segmented model 502. Segmented model 502 may be a three-dimensional model, such as a mesh model, that includes the walls defining the interior lumens or passageways of the lungs.

Based on segmented model 502, centerline segmented model 504 may be generated as shown in FIG. 5B. Centerline segmented model 504 may include a set of three-dimensional straight lines or a set of curved lines that correspond to the approximate center of the passageways contained in segmented model 502. The higher the resolution of segmented model 502, the more accurately the set of straight or curved lines will correspond to the center of the passageways. Representing the lungs with centerline segmented model 504 may provide a smaller set of data that is more efficiently processed by one or more processors or processing cores than the data set of segmented model 502, which represents the walls of the passageways. In this way the functioning of a control system using the model, such as control system 112, may be improved. As shown in FIG. 5B, centerline segmented model 504 includes several branch points, some of which are highlighted for visibility in FIG. 5B. Branch points A, B, C, D, and E are shown at each of several of the branch points. Branch point A may represent the point in the model at which the trachea divides into the left and right principal bronchi. The right principal bronchus may be identified in the centerline segment model 504 as being located between branch points A and B. Similarly, secondary bronchi are identified by branch points B and C and between branch points B and E. Another generation of passageways may be defined between branch points C and D. Each of these generations of passageways may be associated with a representation of the diameter of the lumen of the corresponding passageway. In some embodiments, centerline model 504 may include an average diameter value of each passageway. The average diameter value may be a patient-specific value or a more general value derived from multiple patients.

In some embodiments, segmented model 502 may be used to produce centerline segment 504 or another suitable model including a cloud, set, or collection of points as follows. When segmented model 502 comprises a mesh representing the internal surfaces of one or more passageways, a subset of vertices of a mesh as represented in a stored data file including segmented model 502 may be used. Alternatively, a geometric center of voxels that represent volumes or the passageways in segmented model 502 may be used. Additionally, combinations of various approaches may be used to generate a first set of points, such as centerline segment model 504. For example, a subset of vertices of the mesh may be used along with the geometric center of voxels from the model.

In some embodiments, centerline segmented model 504 is represented in data as a cloud, set, or collection of points in three-dimensional space, rather than as continuous lines. FIG. 5C illustrates centerline segmented model 504 as a set of points 506. Each of the points of the set of model points may include coordinates such as a set of $X_M$, $Y_M$, and $Z_M$ coordinates, or other coordinates that identify the location of each point in the three-dimensional space. In some embodiments, each of the points may include a generation identifier that identifies which passageway generation the points are associated with and/or a diameter or radius value associated with that portion of the centerline segmented model 504. In some embodiments, information describing the radius or diameter associated with a given point may be provided as part of a separate data set.

After centerline segmented model 504 is generated and stored as the set of points 506 shown in FIG. 5C, centerline segmented model 504 may be retrieved from data storage for use in an image-guided surgical procedure. In order to use centerline segmented model 504 in the image-guided surgical procedure, centerline segmented model 504 may be registered to associate the modeled passageways in centerline segmented model 504 with the patient's actual anatomy as present in a surgical environment. Use of the model 504 in point set registration includes using the set of points 506 from centerline segmented model 504.

FIGS. 6A and 6B are exemplary side views of a patient coordinate space including a medical instrument mounted on an insertion assembly. As shown in FIGS. 6A and 6B, a surgical environment 600 includes a patient P is positioned on platform 602. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 600, a point gathering instrument 604 is coupled to an instrument carriage 606. In some embodiments, point gathering instrument 604 may use EM sensors, shape-sensors, and/or other sensor modalities. Instrument carriage 606 is mounted to an insertion stage 608 fixed within surgical environment 600. Alternatively, insertion stage 608 may be movable but have a known location (e.g., via a tracking sensor or other tracking device) within surgical environment 600. Instrument carriage 606 may be a component of a manipulator assembly (e.g., manipulator assembly 102) that couples to point gathering instrument 604 to control insertion motion (i.e., motion along the A axis) and, optionally, motion of a distal end 618 of an elongate device 610 in multiple directions including yaw, pitch, and roll. Instrument carriage 606 or insertion stage 608 may include actuators, such as servomotors, (not shown) that control motion of instrument carriage 606 along insertion stage 608.

Elongate device 610 is coupled to an instrument body 612. Instrument body 612 is coupled and fixed relative to instrument carriage 606. In some embodiments, an optical fiber shape sensor 614 is fixed at a proximal point 616 on instrument body 612. In some embodiments, proximal point 616 of optical fiber shape sensor 614 may be movable along with instrument body 612 but the location of proximal point 616 may be known (e.g., via a tracking sensor or other tracking device). Shape sensor 614 measures a shape from proximal point 616 to another point such as distal end 618 of elongate device 610. Point gathering instrument 604 may be substantially similar to medical instrument system 200.

A position measuring device 620 provides information about the position of instrument body 612 as it moves on insertion stage 608 along an insertion axis A. Position measuring device 620 may include resolvers, encoders, potentiometers, and/or other sensors that determine the rotation and/or orientation of the actuators controlling the motion of instrument carriage 606 and consequently the motion of instrument body 612. In some embodiments, insertion stage 608 is linear. In some embodiments, insertion stage 608 may be curved or have a combination of curved and linear sections.

FIG. 6A shows instrument body 612 and instrument carriage 606 in a retracted position along insertion stage 608. In this retracted position, proximal point 616 is at a position $L_0$ on axis A. In this position along insertion stage 608 an A component of the location of proximal point 616 may be set to a zero and/or another reference value to provide a base reference to describe the position of instrument carriage 606, and thus proximal point 616, on insertion stage 608. With this retracted position of instrument body 612 and instrument carriage 606, distal end 618 of elongate device 610 may be positioned just inside an entry orifice of patient P. Also in this position, position measuring device 620 may be set to a zero and/or the another reference value (e.g., I=0). In FIG. 6B, instrument body 612 and instrument carriage 606 have advanced along the linear track of insertion stage 608 and distal end 618 of elongate device 610 has advanced into patient P. In this advanced position, the proximal point 616 is at a position $L_1$ on the axis A. In some examples, encoder and/or other position data from one or more actuators controlling movement of instrument carriage 606 along insertion stage 608 and/or one or more position sensors associated with instrument carriage 606 and/or insertion stage 608 is used to determine the position $L_x$ of proximal point 616 relative to position $L_0$. In some examples, position $L_x$ may further be used as an indicator of the distance or insertion depth to which distal end 618 of elongate device 610 is inserted into the passageways of the anatomy of patient P.

FIG. 6C is an exemplary side view of patient P in a patient coordinate space including an endotracheal (ET) tube 622. As shown in FIG. 6C, elongate device 610 is inserted through ET tube 622 in order to access one or more passageways of the anatomy of patient P. In some examples, known information about a bend or curvature in ET tube 622 may optionally be used to help locate the position of distal end 618 relative to proximal point 616. In some examples, even when an exact bend or curvature of ET tube 622 is not known, general knowledge about the bend or curvature of ET tube 622 may aid it determining the position of distal end 618 relative to proximal point 616 and/or registering location data collected using elongate device 610 to model information for the passageways of the anatomy of patient P. In some examples, an interior surface 623 of ET tube 622 may optionally include a distinctive color, marking, and/or pattern that may be detectable by an imaging device, such as an endoscopic camera, located at or near distal end 618 of elongate device 610. As distal end 618 enters and/or exits ET tube 622, the change in the distinctive color, marking, and/or pattern relative to interior colors and/or patterns of the passageways may help provide useful location data for distal end 618 and/or elongate device 610.

FIG. 7 is a flowchart illustrating an exemplary method 700 of providing guidance for an image-guided surgical procedure on a patient in a surgical environment, such as surgical environment 600. And although method 700 is described generally in the context of a procedure involving the airways of lungs, it is understood that method 700 is applicable to other anatomical passageways (e.g., blood vessels, ducts, calyces, and/or the like), anatomical passageways in a non-surgical context (e.g., passageways of cadavers, simulated anatomical structures, and/or the like), veterinary passageways, and/or non-medical passageways (e.g., pipes, conduit, ducts, corridors, wells, caves, mines, and/or the like). The method 700 is illustrated in FIG. 7 as a set of operations or processes 702-726. Not all of the illustrated processes 702-726 may be performed in all embodiments of method 700. Additionally, one or more processes that are not expressly illustrated in FIG. 7 may be included before, after, in between, or as part of the processes 702-726. In some embodiments, one or more of the processes 702-726 of method 700 may be implemented, at least in part, in the form of executable code stored on non-transitory, tangible, machine-readable media that when run by one or more processors (e.g., the processors of control system 112) may cause the one or more processors to perform one or more of the processes 702-724.

At a process 702, a relative position and/or orientation of a sensor reference point along an insertion path is calibrated using a position measuring device. In some examples, the proximal point 616 may optionally correspond to the sensor reference point and point gathering instrument 604 of FIGS. 6A and 6B may optionally be used to determine a position and/or orientation of proximal point 616 as instrument carriage 606 moves from a retracted position with proximal point 616 at location $L_0$ to an inserted position with proximal point 616 at location $L_1$. The calibration of proximal point 616 includes determining the direction of the movement of proximal point 616 for each change in position measuring device 620 along axis A. In the embodiments of FIGS. 6A and 6B, where the insertion stage 608 restricts movement of instrument carriage 606 to a linear path, the calibration includes determining the motion along axis A. Using the slope of insertion stage 608 and the position along axis A, the position and orientation of proximal point 616 in surgical environment 600 is determined for each corresponding measurement of position measuring device 620. In some embodiments, where an insertion stage has a curved or otherwise non-linear shape, the calibration includes determining, based on the non-linear shape and the movement of the instrument carriage 606, the position and orientation of proximal point 616 in surgical environment 600. In some examples, calibration of proximal point 616 may optionally be determined by holding distal end 618 of elongate device 610 at a fixed position while instrument carriage 606 is moved along instrument stage 608 and shape sensor 614 is used to determine the geometrical relationship between distal end 618 and proximal point 616. By taking several readings as instrument carriage 606 is moved along instrument stage 608, the position and orientation data collected by shape sensor 614 for proximal point 616 can be correlated with data from position measuring device 620 to calibrate the position and/or orientation of proximal point 616.

At a process 704, passageways of a patient are traversed and location data along the passageways is recorded. An instrument, such as an elongate device, is inserted into and then is moved or traversed along passageways of interest. As the instrument is traversed along the passageways, the position of one or more points associated with the instrument, such as a distal end of the instrument, are monitored and recorded. In the examples of FIGS. 6A and 6B, when distal end 618 of elongate device 610 is traversed along the passageways of patient P, such as along the airways of the lungs of patient P, data from shape sensor 614 and/or one or more other sensors, such as an EM sensor, on elongate device 610 is used to determine the location of distal end 618 and/or other points associated with elongate device 610. This location data may include, and/or be processed to obtain, a set of measured points as described in further detail below. In some examples, selection of the passageways to traverse may optionally be controlled by steering distal end 618 as elongate device 610 is advanced into the passageways using movement of instrument carriage 606 along instrument stage 608. In some examples, the steering of distal end 618 may optionally be controlled via teleoperational, manual, and/or automated control, such as by using master assembly 106, to survey and obtain location data for a portion of the passageways. In some examples, the steering of distal end 618 may optionally include adjusting a roll, a pitch, and/or a yaw of distal end 618, such as is described with respect to the dashed line depictions 219 of distal end 218 in FIG. 2A. As distal end 618 of elongate device 610 is moved within the passageways, the location of the distal end 618 and/or other points associated with elongate device 610 are gathered at multiple positions of distal end 618 and/or elongate device 610. In some embodiments when the passageways correspond to airways of lungs, distal end 618 of elongate device 610 may be extended up to at least 75 mm or farther into the passageways. In some examples, distal end 618 of elongate device 610 may optionally be extended through or into multiple branched generations, such as three or more branched generations on each side of the lung. The number of generations accessible with elongate device 610 may increase as the diameter of elongate device 610 decreases and/or as the flexibility of elongate device 610 increases.

In some embodiments, as elongate device 610 is traversed along the passageways and the location data is collected, the location data may be subject to one or more sources of noise that may result in inaccurate location data being collected. In some examples, movement in the locations of the passageways due to motions and/or forces independent of elongate device 610 may occur. In some examples, this movement may occur as a result of motion by the patient, anatomic motions such as respiration, and/or the like. In some examples, a position of elongate device 610 within a larger passageway may not correspond with the centerline of the passageway, such as may correspond to the centerline in centerline segmented model 504. In some examples, elongate device 610, itself, may introduce noise as it collides with and potentially moves, distorts, and/or reshapes the flexible walls that are common in, for example, the passageways of the anatomy of a patient. In some embodiments, using a location data collection process that reduces and/or eliminates these and other sources of noise is desirable. In some examples, collecting location data at a same time along the length of elongate device 610 may achieve these goals. In some examples, the effects of the motion of the patient and the anatomic motion may be reduced by collecting multiple points of location data at the same time as each of the collected points would be subject to roughly the same motion effects. In some examples, the effects of the movement of the walls of the passageway due to elongate device 610 may similarly be reduced.

FIG. 8 illustrates a flowchart of an exemplary method 800 of recording passageway location data. And although method 700 is described generally in the context of a procedure involving the airways of lungs, it is understood that method 700 is applicable to other anatomical passageways (e.g., blood vessels, ducts, calyces, and/or the like), anatomical passageways in a non-surgical context (e.g., passageways of cadavers, simulated anatomical structures, and/or the like), veterinary passageways, and/or non-medical passageways (e.g., pipes, conduit, ducts, corridors, wells, caves, mines, and/or the like). The method 800 is illustrated in FIG. 8 as a set of operations or processes 802-812. Not all of the illustrated processes 802-812 may be performed in all embodiments of method 800. Additionally, one or more processes that are not expressly illustrated in FIG. 8 may be included before, after, in between, or as part of the processes 802-812. In some embodiments, one or more of the processes 806, 808, and/or 812 are optional and may be omitted. In some embodiments, one or more of the processes 802-812 of method 800 may be implemented, at least in part, in the form of executable code stored on non-transitory, tangible, machine-readable media that when run by one or more processors (e.g., the processors of control system 112) may cause the one or more processors to perform one or more of the processes 802-812.

At a process 802, an elongate device is traversed along passageways. In some examples, an elongate device, such as elongate device 610, is inserted and then moved or traversed along passageways, such as the airways of the lungs of a patient. In some examples, a distal end of the elongate device may be inserted into and then advanced and/or retreated along the passageways by advancing and/or retracting a proximal end of the elongate device which is mounted to an instrument carriage, such as instrument carriage 606. In some examples, selection of the passageways to traverse may optionally be controlled by steering the distal end as the elongate device is advanced into the passageways. In some examples, the steering of the distal end of the elongate device may optionally be controlled via manual control, automated control, and/or teleoperational control such as by using master assembly 106. In some examples, the steering of the distal end of the elongate device may optionally include adjusting a roll, a pitch, and/or a yaw of the distal end of the elongate device, such as is described with respect to the dashed line depictions 219 of distal end 218 in FIG. 2A.

At a process 804, a data collection event is detected. As the elongate device is traversed along the passageways during process 802, it is advantageous to collect the location data on the passageways at certain instances during the traversal that yield a useful quantity of location data to support, for example, a registration procedure. In some embodiments, one or more manual, semi-automatic, and/or automatic criteria may be used to determine when a suitable data collection event is to occur.

In some examples, a data collection event may occur instantaneously, triggering the immediate collection of position data from one or more sensors on the elongate device, the data collection event may trigger the collection of data starting at the detection of the event and for a certain time interval going forward, or the event may trigger the immediate collection of data but additional use of previous position data stored in a buffer or data stored over some time interval. In some examples, data may be collected continuously as the elongate device traverses the passageways but the data collection event may provide an indicator that data collected during a time interval encompassing the data collection event is used for analysis, such as for registration. In some examples, analyzed data can include data captured during an interval, for example 1 second before and 1 second after a data collection event, then the analyzed data may be averaged and used for registration. In some examples, the time interval may be chosen to cover an anatomic cycle, such as a respiration cycle, a heartbeat cycle, and/or the like.

In some examples, a data collection event may optionally be detected by monitoring motion of the elongate device along a longitudinal axis of the elongate device, such as the A axis of FIGS. 6A and 6B, which can be referred to as insertion motion. Insertion motion may be in either the insert direction (movement advancing the elongate device within passageways) or retract direction (movement retracting the elongate device from the passageways). In some examples, the insertion motion may be detected using tracking sensors (such as optical sensors, position sensors, encoders, and/or the like) on an instrument carriage, such as instrument carriage 606, to which the elongate device is mounted. In some examples, the insertion motion may be detected using a shape sensor, such as shape sensor 222 and/or shape sensor 614, which is integrated in the elongate device. The shape sensor may be interrogated to determine a shape of the shape sensor and accordingly a shape of the elongate device. In some examples, the elongate device may be inserted through a known fixture with a known shape, such as an endotracheal tube or a fixture external to a patient. The shape of a distal portion of the elongate device is measured to match a shape of the endotracheal tube. As the elongate device is inserted further, the distal portion of the elongate device is measured to match a shape of a passageway, while a proximal portion of the elongate device is measured to match the shape of the endotracheal tube. In this manner, motion of the elongate device may be detected. In some examples, an imaging device, such as an endoscopic camera, coupled to the elongate device may be used to detect insertion motion as objects, such as anatomical features, are viewed as larger or smaller. In some examples, insertion motion may also be detected by viewing the elongate device using external imaging such as fluoroscopy, computed tomography (CT), magnetic resonance imaging (MRI), thermography, ultrasound, optical coherence tomography (OCT), thermal imaging, impedance imaging, laser imaging, nanotube X-ray imaging, and/or the like.

In some examples, a data collection event may optionally be detected by monitoring an insertion depth of the elongate device and triggering collection of location data when the insertion depth reaches a local maximum. In some examples, the insertion depth of the elongate device is monitored by tracking a position of the instrument carriage to which the elongate device is mounted. In some examples, a local maximum corresponds to instances where a velocity of the instrument carriage indicates that the instrument carriage has transitioned to being retracted away from the patient (e.g., when the velocity first becomes negative or becomes more negative than a nominal negative threshold, such as approximately −1 mm/s or so). In some examples, the greatest insertion depth is recorded and when a current insertion depth is more than a small threshold distance (e.g., approximately 5 mm or so) below the greatest insertion depth a local maximum occurs. In some examples, the recording of the greatest insertion depth is restarted when the elongate device is transitioned back to being inserted. In some examples, a data collection event may optionally be triggered when the insertion depth is above an insertion threshold, such as 75 mm or longer. In some examples, data collection may be triggered once the elongate device diverges from a previously navigated path in which data was previously collected. Accordingly, the data collection event may be triggered by detecting a change in steering direction of the elongate device above a specified threshold, as measured by the shape sensor. In some examples, the divergence from a path may be detected by a change in steering direction and a change in direction of insertion motion of the elongate device along with a change in a steering direction of the elongate device. In some examples, an elongate device may retract from a first passageway, then change direction and begin inserting into a second passageway. The data collection event may be triggered by detecting the change in insertion motion direction from retract to insert and a change in steering motion of the elongate device into the second passageway.

In some examples, the data collection event may optionally be triggered when a change in direction during the insertion motion is detected, i.e. the elongate device transitions from insertion to retraction or retraction to insertion. A change in direction may be detected by a change in velocity or a change in position of the elongate device. In some examples, a data collection event may optionally be triggered when insertion and/or retraction movement of the elongate device is paused for more than a minimum period of time, such as approximately 2 s or longer.

In some examples, a data collection event may optionally be triggered manually by the operator of the elongate device, such as operator O, by activating one or more controls and/or commands using a master assembly. In some examples, semi-automated data-collection may proceed by asking the operator to traverse a certain path at which point data may be collected continuously or at a critical insertion depth. In some examples, an imaging device, such as an endoscopic camera, may be used to trigger data collection either by detecting a key anatomical feature, by sensing proximity of the distal tip to an anatomical feature such as a lumen wall, and/or the like. In some examples, more than one mechanism for detecting a data collection event may optionally be used during process 804. In some examples, combinations of two or more triggering mechanisms for a data collection event may optionally be combined, such as detection of a local maximum in the insertion depth when the insertion depth is above the insertion threshold.

At an optional process 806, anatomic phase is accounted for. When the passageways being traversed during process 802 correspond to passageways within a patient, significant fluctuations in the location of the elongate device may occur due to automatic bodily movements, such as movements caused by respiration, heart beats, and/or the like. Because these bodily movements can change the location of the elongate device, these bodily movements may introduce significant noise in the location data being collected. However, because the bodily movements are typically cyclical (e.g., inhalation-exhalation, heart rhythm, etc.), making the collection of the location data while accounting for the phase within each cycle may significantly reduce noise introduced by the bodily movements. In some examples, the anatomic phase may be detected using a respiratory monitor, monitoring an artificial respirator, monitoring an electro-cardiogram of the patient, monitoring thoracic movement of the patient using a movement pad, and/or the like. In some examples, the anatomic phase may optionally be accounted for by noting the anatomic phase when the location data is collected and recording the anatomic phase with the location data so that later analysis may organize and/or sort the location data based on the anatomic phase. In some examples, the anatomic phase may optionally be accounted for by delaying the collection of the location data until the anatomic cycle reaches a target anatomic phase and/or a target range of anatomic phases and then optionally tagging the location data with the anatomic phase when the location data is collected. In some examples, an extrinsic model of respiratory motion may be employed to apply an automatic correction to collected data at the given respiratory phase. The extrinsic model may be derived from multiple pre-operative CTs, intraoperative imaging modalities such as fluoroscopy, and/or the like.

At an optional process 808, external forces on the elongate device are minimized. As the elongate device is traversed along the passageways during process 802, the elongate device may come into contact with one or more walls of the passageways. When the one or more walls of the passageways are flexible, as is common with passageways within the anatomy of a patient, the elongate device may alter the location of the one or more walls, which may introduce unwanted noise in the location data being collected. In some examples, the extent to which the elongate device may be altering the location of the one or more walls may optionally be reduced by monitoring external forces applied to the exterior of the elongate device by the one or more walls and adjusting the position of the elongate device to reduce these external forces. In some examples, the external forces may optionally be monitored using force and/or pressure sensors, such as strain gauges, located at various locations along the exterior of the elongate device. In some examples, an external force detected by a force and/or pressure sensor may optionally be compensated for by flexing a corresponding region of the elongate device away from the external force. In some examples, an overall external force detected by the force and/or pressure sensors may optionally be compensated for by adjusting the insertion depth of the elongate device, adjusting the steering of the distal end, and/or the like and/or any combination of these approaches.

At a process 810, points along a shape sensor are simultaneously collected. In some examples, the shape sensor, such as shape sensor 222 and/or shape sensor 614, is interrogated to determine a shape of the shape sensor. The shape of the shape sensor along with knowledge of a proximal point on the shape sensor is then used to determine the locations of points along the length of the shape sensor. Each of these points describes a position within the passageway taken at roughly the same instant in time so that variations in the locations of the passageways due to anatomic phase, forces applied by the elongate device to the wall of the passageway, and/or other noise sources that vary over time may be greatly reduced. Each of the points along the length of the shape sensor are then collected and optionally stored as the collected location data.

At an optional process 812, the captured points are adjusted based on the location of the shape sensor relative to the elongate device. In some examples, the location of the shape sensor relative to the elongate device may not be very representative of location data corresponding to, for example, the centerline of the passageways. In some examples, when the shape sensor is located away from a centerline of the elongate device, such as on the exterior of the elongate device and/or in an interior region of the elongate device that does not correspond to the centerline of the elongate device, each of the points collected during process 810 may be adjusted so that they more accurately reflect the centerline of the elongate device, and thus the centerline of the passageways. In some examples, the shape sensor may be used to generate a dataset of points along the full length of the elongate device. In some examples, the known geometric relationship between the shape sensor and the rest of the elongate device is used to adjust the locations of the points collected during process 810. After the locations of the points are adjusted they are stored as the collected location data.

After the collection of location data during process 812, method 800 may optionally be repeated by returning to process 802, traversing the elongate device along the passageways to another location, and then repeating the collection of location data.

As discussed above and further emphasized here, FIG. 8 is merely an example which should not unduly limit the scope of the claims. One of ordinary skill in the art would recognize many variations, alternatives, and modifications. In some embodiments, additional factors may be used to adjust the captured points. In some examples, the external forces detected during process 808 may be used to adjust the captured points. In some examples, detecting external forces on one side of the elongate device and not on another may indicate that the elongate device is to one side of a passageway so that the centerline of the passageway may be different from the centerline of the elongate device. In some examples, information about a size of the passageway included in the model information received during process 706 in combination with the detected force may be used to offset the captured points based on a difference between a size of the elongate device and a size of the passageway.

FIG. 9 illustrates exemplary location data collected by traversing airways in human lungs. As shown in FIG. 9, location data collected by process 704 and/or method 800 is depicted by data points D. In some examples, the data points D may be stored in memory as data sets or point pools with coordinates, timestamps, sensor IDs, anatomic phase information, insertion depth, and/or the like. The data points D may correspond to location data for distal end 618 and/or other points associated with elongate device 610 collected using shape sensor 614 and/or one or more other sensors as distal end 618 is advanced into and/or retracted from the passageways being traversed. In the examples of FIGS. 6A and 6B, the location of a given collected data point $D_X$ in surgical environment 600 is determined by combining information from position measuring device 620 and the shape data from shape sensor 614 and/or one or more other sensors when distal end 618 and/or some other point associated with elongate device 610 is located at the point $D_X$. In some examples, the position $L_X$ of proximal point 616 along instrument stage 608 as aided by the calibration of process 702 and data from shape sensor 614 may optionally be used to determine the location of point $D_X$. The location in the surgical environment coordinate space for the data points D becomes a reference set of location data for the passageways that can be registered with location data from a model of the passageways as is described in further detail below.

Referring back to FIG. 7, at an optional process 706, landmark data for the passageways is recorded. In some examples, one or more of the gathered data points D may correspond to one or more landmark locations within the passageways. In some examples, the gathered data points D that correspond to the one or more landmark locations may optionally be used to seed a registration process, such as an ICP process. In some examples, each of the gathered data points D that corresponds to the one or more landmark locations may be referred to as seed points. In some examples, the gathered data points D that correspond to the one or more landmark locations may be tagged with a landmark indicator when those data points D are stored in memory. In some examples, the one or more landmark locations may correspond to branch points in the passageways. In some examples, when the passage ways are airways in lungs, the one or more landmark locations may correspond to carinas within the lungs.

In some examples, designation of the data points D as corresponding to the one or more landmark locations may occur as a result of input from an operator, such as operator O, and/or through one of more other approaches and/or automated algorithms. In some examples, the operator may designate data points D as corresponding to the one or more landmark locations by pressing a button, a pedal, a lever, issuing a command recognizable with voice recognition, and/or the like and/or activating an appropriate input control on a master assembly, such as master assembly 106. In some examples, the operator may navigate the distal end of the elongate device to a point in proximity to one of the landmark locations and initiate physical contact between the distal end and a wall of the passageways. In some examples, a torque sensor and/or an encoder for an actuator controlling the distal end may register resistance and/or a force against the distal end due to the contact with the wall of the passageway and trigger the tagging of the current location of the distal end as a landmark location. In some examples, a touch sensor, such as a capacitive and/or a Hall effect sensor, may be positioned near the distal end of the elongate device to provide an indication when the distal end is close to or in contact with the wall of the passageways and trigger the tagging of the current location of the distal end as a landmark location.

In some examples, when the distal end of the elongate device is passed through an ET tube, such as ET tube 622, a known bend or curvature of the ET tube may aid in the identification of one or more of the landmark locations. In some examples, even when the bend or curvature in the ET tube is not precisely known, the bend or curvature may be sufficiently distinctive to be identified as corresponding to a specific region of the passageways, such as the upper respiratory tract and trachea because a more proximal portion of the elongate device at a proximal end of the ET tube forms a nearly 90° angle with respect to a more distal portion of the elongate device at a distal end of the ET tube. Based on pose information of the proximal point of the elongate device and the curvature of the ET tube, which may be easily identified using the shape sensor, the trachea of the patient may be identified and used as one of the landmark locations. In some examples, detection and location of the distal end of the ET tube, such as by detecting the end of a distinctive color, marking, and/or pattern of an interior surface of the ET tube, may further aid in identifying a landmark location within the trachea of the patient.

According to some embodiments, when the orientation of the patient relative to the proximal point of the elongate device is known, navigation of the distal end of the elongate device to the left or the right may help identify one or more landmark locations associated with the left and/or right primary bronchus. In some examples, data from the shape sensor and/or other sensor may optionally be used to identify the roughly right angle between the proximal end and the distal end of the ET tube created by the curvature of the ET tube, with the distal end of the ET tube identifying a possible landmark location within the trachea of the patient. In some examples, the roughly right angle may optionally be used to identify a first plane that bisects the anatomy of the patient into right and left halves. As the distal end is further steered into either the left or right primary bronchus, a second angle defining a second plane may be identified, which is roughly orthogonal to the first plane. The orientation of the first and second planes may then be used to determine one or more additional landmark locations.

At a process 708 model information for the passageways is received. In some examples, pre-operative and/or intra-operative images of the passageways, such as the images obtained using process 542, may be used to construct the model of the passageways. In some examples, the model of the passageways may be generated by segmenting the pre-operative and/or intra-operative images using processes 454. In some examples, the model information for the passageways may correspond to the centerline segmented model 504 as described in FIG. 5C.

At an optional process 710, an initial seed transformation between the landmark data and the model information for the passageways is determined. According to some embodiments, use of a suitable seed transformation for close point registration algorithms, such as ICP often result in better registration and/or faster convergence for the close point algorithm. In some examples, the transformation that maps between the landmark locations identified in the landmark data during process 706 and the corresponding locations in the model information received during process 708 often provides a good seed transformation for close point registration between the location data collected during process 704 and/or method 800 and the model information received during process 708. In some examples, the initial seed transform may optionally be a rigid transform in which each of the data points D for the landmark locations are transformed by the same coordinate transformation that maps positions and orientations from a coordinate system of the location data collected during process 704 and/or method 800 and a coordinate system for the model information received during process 708. In some examples, the initial seed transformation may optionally be a non-rigid transformation where each of the data points D for the landmark locations are transformed by different coordinate transformations. In some examples, the initial seed transformation may be modeled as a homogenous transform that can translate and/or rotate 3D points from one coordinate system to another. In some examples, multiple initial seed transformations determined using different landmark data and/or different landmark locations may optionally be compared with the initial seed transformation having the smallest error when mapping between the coordinate system of the location data collected during process 704 and/or method 800 and the coordinate system for the model information received during process 708 being selected as the initial seed transformation. In some examples, the first and second planes determined during process 706 may optionally be used to determine the initial seed transformation.

At an optional process 712, the initial seed transformation is applied to the recorded location data. Using the rigid or non-rigid transformation determined during process 710, the location data collected and recorded during process 704 and/or method 800 is transformed to place the points in the location data in closer alignment with corresponding points in the model information received during process 708. In some examples, when the initial seed transformation is a homogeneous transformation, the transformation of the location data is accomplished by applying the initial seed transformation to each of the points in the location data using matrix multiplication.

At a process 714, the location data recorded during process 704 and/or method 800 is registered to the model information received during process 708. Process 714 is shown as an iterative process that includes repeated application of processes 716-722 until convergence between the location data and the model information is obtained. In some examples, the iterative processes of process 714 correspond to the ICP registration technique. FIG. 9 illustrates an exemplary post registration alignment of two sets of points resulting from application of process 714 to the location data as collected and shown in FIG. 9. In some embodiments, the location data used during the registration may optionally be limited to location data collected during a particular anatomic phase (or a range of anatomic phases) so as to limit the effects of noise introduced in the collected data by changes in the anatomic phase.

At a process 716, points in the location data are matched to points in the model information. Transformation of the points in the location data using the initial seed transformation during process 712 and/or by the transformation of process 720 as described further below typically brings the points in the location data into better positional and/or rotational alignment with corresponding points in the model information. However, because initial iterations to bring the points in the location data in alignment with corresponding points in the model information do not always identify the correct correspondence between the points in the location data and the points in the model information, rematching to update the correspondence is performed. Each of the points in the location data, as transformed, is matched to a point in the model information that is closest to the point in the location data. In some examples, the closest point in the model information may be determined by iterating through each of the points in the model information and finding the point that has a shortest Euclidean distance to the point in the location data being matched. In some examples, other techniques, such as KD trees and/or the like may optionally be used to more efficiently perform the matching. In some examples, some matches may be discarded based on a maximum distance threshold determination, a maximum angle threshold determination, and/or other metrics employed to filter out matches that are not deemed to be reliable enough or "close" enough for inclusion in the transformation determined during a process 718 as is described further below.

At the process 718, a further transformation is determined. Based on the matching of process 716, the further transformation identifies an additional transformation to the location data to bring the location data into further alignment with the model information. In some examples, the further transformation determines a displacement and/or rotation, such as in the form of a homogenous transformation, which would best bring the matched points into alignment. In some examples, the further transformation is determined by computing an overall and/or an aggregated offset in position and orientation between the points matched during process 716. In some examples, the further transformation may be limited such that a maximum offset and/or a maximum rotation is applied during any iteration of process 714. In some examples the maximum offset and/or the maximum rotation may optionally be scaled based on a number of iterations of process 714 that have been performed.

At a process 720, the further transformation is applied to the location data. Using the further transformation determined during process 718, the location data as transformed by process 712 and/or prior applications of process 720 is further transformed to place the location data in closer alignment with the points in the model information received during process 708. In some examples, when the further transformation is a homogeneous transformation, the further transformation of the location data is accomplished by applying the further transformation to each of the points in the location data using matrix multiplication.

At a process 722, the convergence of the registration technique is evaluated. In some examples, error measures between the locations of the points in the location data and the locations of the points in the model information are computed that assess an overall difference between the location data as transformed and the model information. When the error measures in aggregate are greater than a threshold value, additional iterations of processes 716-722 are repeated until the overall error measures fall below the threshold value. A result of this process is illustrated in FIG. 10 showing how multiple iterations of processes 716-722 are able to bring the location data as represented by points D in FIG. 9 into alignment with the points in anatomic model information 550. In some examples, a number of iterations to converge between FIG. 9 and FIG. 10 may vary based on differences between the model information and the actual point locations in the location data, the convergence threshold, and/or the like.

In some embodiments, the progression of processes 716-722 may optionally be displayed to an operator, such as operator O, by displaying images similar to FIGS. 8 and 9 on a user interface display. In some examples, the operator may optionally monitor the registration to determine when adequate convergence is achieved. In some examples, the registration of processes 716-722 may optionally be repeated during a surgical procedure such as at regular intervals, as additional location data is obtained, when the patient is moved, and/or the like.

After the registration is complete, an image-guided surgical procedure may, optionally, be performed. In some examples, the model information may identify one or more intervention sites and/or targeted locations in the anatomy of the patient to which a targeted procedure is to be applied. In some examples, a composite transformation including the initial seed transformation determined during process 710 and each of the further transformations determined during process 718 may be used to map current location data for the distal end of the elongate device to a corresponding location in the model information to aid the operator in planning and/or executing a motion plan to move the distal end of the elongate device from its current location to one of the targeted locations. As shown in FIG. 7, the image-guided surgical procedure may correspond to optional processes 724 and 726.

At the optional process 724, a current location of the distal end of the elongate device is determined. In some examples, the location of the proximal point and data from the shape sensor may be used to determine the current location of the distal end of the elongate device where a surgical instrument can be applied to the anatomy of the patient by inserting the surgical instrument through the elongate device. In some examples, other sensors, such as the EM sensor may optionally be used to determine the current location of the distal end of the elongate device.

At the optional process 726, the distal end of the elongate device is located in the model information. Using the composite transformation determined by processes 702-722, the current location of the distal end of the elongate device determined during process 724 may be transformed so that the location of the distal end of the elongate device, and thus the surgical instrument may be determined relative to the model information. Once the location of the distal end of the elongate device is known within the passageways as described in the model information, it is possible for the operator and/or an automated system to plan and/or execute a motion plan to deliver the surgical instrument to one of the targeted locations. As the plan is executed, processes 724 and 726 may be repeated to continually update the current location of the distal end of the elongate device and the motion plan.

As discussed above and further emphasized here, FIG. 7 is merely an example which should not unduly limit the scope of the claims. One of ordinary skill in the art would recognize many variations, alternatives, and modifications. In some embodiments, the transformation of processes 712 and/or 720 may be applied in different ways. In some examples, the initial seed transformation and/or the further transformation may optionally be defined to transform the points in the model information so that they are in closer alignment with the points in the location data with the initial seed transformation and/or the further transformation being applied to transform the model information rather than the location data. In some examples, the initial seed transformation and/or the further transformation may optionally be divided into separate transformations designed to transform both the location data and the model information toward a common coordinate system.

One or more elements in embodiments of the invention (e.g., the processes of methods 700 and/or 800) may be implemented in software to execute on a processor of a computer system, such as control system 112. When implemented in software, the elements of the embodiments of the invention are essentially the code segments to perform the necessary tasks. The program or code segments can be stored in a non-transitory machine-readable storage media, including any media that can store information including an optical medium, semiconductor medium, and magnetic medium. Machine-readable storage media examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical device, comprising:
an elongate device including a steerable distal end and a shape sensor located along a length of the elongate device; and
one or more processors coupled to the elongate device;
wherein while the elongate device is being traversed through one or more passageways of a patient, the one or more processors are configured to:
based on information from a sensor, monitor an insertion motion of the elongate device;
detect a data collection event, wherein the data collection event is at least partially based on a change in direction of the insertion motion of the elongate device; and
capture, in response to detecting the data collection event, a plurality of points along the length of the elongate device using the shape sensor.

2. The medical device of claim 1, wherein the shape sensor is a fiber optic shape sensor.

3. The medical device of claim 1, wherein the elongate device is traversed through the one or more passageways of the patient using one or more actuators to perform one or more of insert, retract, or steer the elongate device.

4. The medical device of claim 1, further comprising the sensor, wherein the sensor comprises a tracking sensor coupled to a proximal end of the elongate device.

5. The medical device of claim 1, wherein the one or more processors are configured to monitor the insertion motion of the elongate device including monitor a current insertion depth of the elongate device and wherein the data collection event is detected when the current insertion depth of the elongate device is beyond a threshold insertion depth, no change of the current insertion depth of the elongate device is detected for longer than a threshold period of time, or the current insertion depth of the elongate device is beyond a threshold retraction distance.

6. The medical device of claim 1, wherein the one or more processors are configured to monitor the insertion motion of the elongate device including monitoring the change in direction of the insertion motion of the elongate device and wherein the data collection event is detected during the change in direction.

7. The medical device of claim 1, wherein the one or more processors are configured to detect the data collection event further based on detecting at least one of a change in path of the elongate device or a manual triggering of data collection by an operator.

8. The medical device of claim 1, further comprising an imaging device coupled to the elongate device.

9. The medical device of claim 8, wherein the one or more processors are configured to detect the data collection event further based on detecting a feature in images captured by the imaging device.

10. The medical device of claim 1, wherein the one or more processors are further configured to determine an anatomic phase of the patient when the data collection event is detected and tag each of the plurality of points with the determined anatomic phase.

11. The medical device of claim 1, further comprising one or more force or pressure sensors located along the length of the elongate device, wherein the one or more force or pressure sensors comprises at least one of the shape sensor or a strain sensor.

12. The medical device of claim 11, wherein the one or more processors are further configured to:
determine one or more external forces on the elongate device using the one or more force or pressure sensors; and
provide instructions to adjust a position of the elongate device to reduce the one or more external forces on the elongate device before capturing the plurality of points.

13. The medical device of claim 1, wherein the shape sensor is located at a distance from a centerline of the elongate device and wherein the one or more processors are configured to offset locations of the plurality of points based on the location of the shape sensor relative to the centerline of the elongate device.

14. The medical device of claim 1, wherein the one or more processors are further configured to register the plurality of points to a model of the passageways of the patient.

15. A method, comprising:
traversing an elongate device through one or more passageways, the elongate device having a shape sensor located along a length of the elongate device;
based on information from a sensor, monitoring an insertion motion of the elongate device within the one or more passageways;
detecting, using one or more processors, a data collection event, wherein the data collection event is at least partially based on a change in direction of the insertion motion of the elongate device; and
capturing, by the one or more processors, in response to detecting the data collection event, a plurality of points along the length of the elongate device using the shape sensor.

16. The method of claim 15, further comprising reducing one or more external forces on the elongate device before capturing the plurality of points.

17. The method of claim 16, wherein reducing the one or more external forces on the elongate device comprises:
determining the one or more external forces using one or more force or pressure sensors located along the length of the elongate device; and
adjusting a position of the elongate device based on the one or more external forces;
wherein adjusting the position of the elongate device comprises using one or more actuators to steer the elongate device, insert the elongate device, retract the elongate device, or any combination thereof.

18. A non-transitory machine-readable medium comprising a plurality of machine-readable instructions which when executed by one or more processors associated with a medical device are adapted to cause the one or more processors to perform a method comprising:
monitoring an insertion motion of an elongate device while the elongate device is being traversed through one or more passageways of a patient, the elongate device having a steerable distal end and a shape sensor located along a length of the elongate device;

detecting a data collection event, wherein the data collection event is at least partially based on a change in direction of the insertion motion of the elongate device; and capturing, in response to detecting the data collection event, a plurality of points along the length of the elongate device using the shape sensor.

19. The non-transitory machine-readable medium of claim 18, wherein monitoring the insertion motion of the elongate device includes measuring an insertion depth of the elongate device, detecting no change in insertion depth of the elongate device for longer than a threshold period of time, or detecting a change in direction of the insertion motion.

20. The non-transitory machine-readable medium of claim 18, further comprising:

determining an anatomic phase of the patient when the data collection event is detected; and tagging each of the plurality of points with the determined anatomic phase or delaying capturing of the plurality of points until the anatomic phase of the patient is a predetermined anatomic phase.

\* \* \* \* \*